United States Patent [19]

Anapliotis et al.

[11] Patent Number: 5,007,910
[45] Date of Patent: Apr. 16, 1991

[54] DEVICE FOR COMPRESSION SCREWING

[76] Inventors: Emmanuel Anapliotis, Kiebitzweg 5, D-1000 Berlin 33; Gernot Regener, Bocksfeldstrrasse 1e, D-1000 Berlin 20; Uwe Ahrens, Nürnberger Strasse 46, D-1000 Berlin 30; Hermann Jehle, Kreiskrankenhaus Alte Waibstädter Str. 2, D-6920 Sinsheim, all of Fed. Rep. of Germany

[21] Appl. No.: 453,289

[22] Filed: Dec. 22, 1989

[30] Foreign Application Priority Data

Jan. 4, 1989 [DE] Fed. Rep. of Germany ... 8900121[U]

[51] Int. Cl.$^5$ .............................................. A61F 5/04
[52] U.S. Cl. ............................................ 606/65; 606/66
[58] Field of Search ............... 606/53, 60, 62, 65–67, 606/72, 73

[56] References Cited

U.S. PATENT DOCUMENTS

| | | | |
|---|---|---|---|
| 3,996,931 | 12/1976 | Callender, Jr. ........................ | 606/65 |
| 4,438,762 | 3/1984 | Kyle ...................................... | 606/65 |
| 4,612,920 | 9/1986 | Lower ................................... | 606/66 |
| 4,621,629 | 11/1986 | Koeneman ........................... | 606/65 |
| 4,657,001 | 4/1987 | Fixel ..................................... | 606/66 |

FOREIGN PATENT DOCUMENTS 0085493 8/1983 European Pat. Off. .

Primary Examiner—Robert A. Hafer
Assistant Examiner—Kerry Owens
Attorney, Agent, or Firm—Spencer & Frank

[57] ABSTRACT

Device for compression screwing fractures of the femural neck, consisting of a plate of a sleeve, the sleeve being hollow and cylindrical in shape, the plate of the sleeve being attached by screws to the femur shaft and of a bone screw being located within the sleeve which is provided with a female thread on its head side into which a compression screw having a respective male thread fits, whereby the compression screw is supported by means of the bottom edge of its head or by a respective, especially conical contact surface for the limitation of its movement against a fixing ring being located within the sleeve in such a way that it can be displaced, sliding with its surface along the inner surface of the sleeve and having a conical surface in an axial direction that is adapted to the bottom edge of the head of the compression screw and the cone angle of which is sized in such a way that the adhesive friction between the outer surface of the fixing ring and the inner surface of the sleeve is greater than the compressional force acting in the longitudinal direction of the screw.

6 Claims, 1 Drawing Sheet

5,007,910

DEVICE FOR COMPRESSION SCREWING

CROSS REFERENCE TO RELATED APPLICATION

This application claims the priority of the Federal Republic of Germany application No. G 89 00 121.4 filed Jan. 4th, 1989, which is incorporated herein by reference.

BACKGROUND OF THE INVENTION

The present invention relates to a device for compression screwing fractures of the femoral neck, consisting of a plate of a sleeve, the sleeve being hollow and cylindrical in shape, the plate of the sleeve being attached by screws to the femur shaft and of a bone screw being located within the sleeve which is provided with a female thread on its head side into which a compression screw having a respective male thread fits.

In the case of fractures of the femoral neck, osteosynthesis is gradually taking over from bone replacement with endoprostheses. This shift has led to the development of numerous new operation methods and new instruments.

The screwing and/or nailing together of bone fragments in particular, is used widely and has shown that a pressural force which causes the fracture surfaces to notch or wedge into each other greatly improves the healing of the fracture. In particular, the revascularization of the top fragment is greatly improved due to the better stability and the prevention of destructive shear and rotational movement in such a mechanically endangered area. It is known to construct the inner side of the sleeve of such a compression screw in a step-like fashion so that the head of the compression screw is supported by the ring-shaped face-end of the milled opening. As the screwing length of the bone screw depends on the type and position of the fracture it can vary greatly and the length of the compression screw must be adapted to the actual conditions every time when using a fixed support surface.

This has the disadvantage that if a too short or a too long compression screw is selected it has to be screwed back out again in order to replace it with a screw of the right length. The patient is thus additionally subjected to unnecessary strain.

SUMMARY OF THE INVENTION

It is an object of the invention to provide a device for compression screwing of the above mentioned type with which uniform compression screws can be used and also have a safe support in the sleeve which in turn can withstand large axial forces.

The above and other objects are accomplished according to the invention by utilizing the realization that a length selection or adaptation of the screw is no longer necessary if a fixing ring is placed into the sleeve in any position which then widens when the compression screw is tightened and is pressed so tightly against the inner surface of the sleeve that the adhesive friction prevents the fixing ring from sliding. The fixation is achieved by axially and conically twisting out the fixing ring until the bottom edge of the head of the compression screw exactly fits into it. The widening of the fixing ring can be augmented according to a favorable further embodiment of the invention by slitting the fixing ring in a longitudinal direction. The fixing ring can also be positioned and secured against unintentional sliding in the sleeve whilst the sleeve is being inserted because of its springlike characteristics in the radial direction.

It is also particularly advantageous that the construction of the device for compression screwing according to the invention does not enlargen it. The device is not expensive and can be constructed economically without an appreciable increase in the cost as, in particular, the amount of raw material required can in some cases decrease due to the shorter screws. The head of the compression screws rests inside the sleeve and therefore is of a smaller diameter.

In order to prevent the fixing ring from being able to turn whilst the compression screw is being screwed in, it preferably has an outer longitudinal groove. The inside of the sleeve has a corresponding projection in the form of a bar which slots into the groove of the fixing ring. Alternately the sleeve can have a groove into which a pin or a projection of the fixing ring can slot.

In order to ensure tissue compatibility it has also proven to be advantageous to construct all the parts of the implantate and all the instruments that come into contact with the tissue out of the one same material, in particular out of the body compatible steel X 5 CrNiMo 1810.

DESCRIPTION OF THE PREFERRED EMBODIMENT

Figure 1:
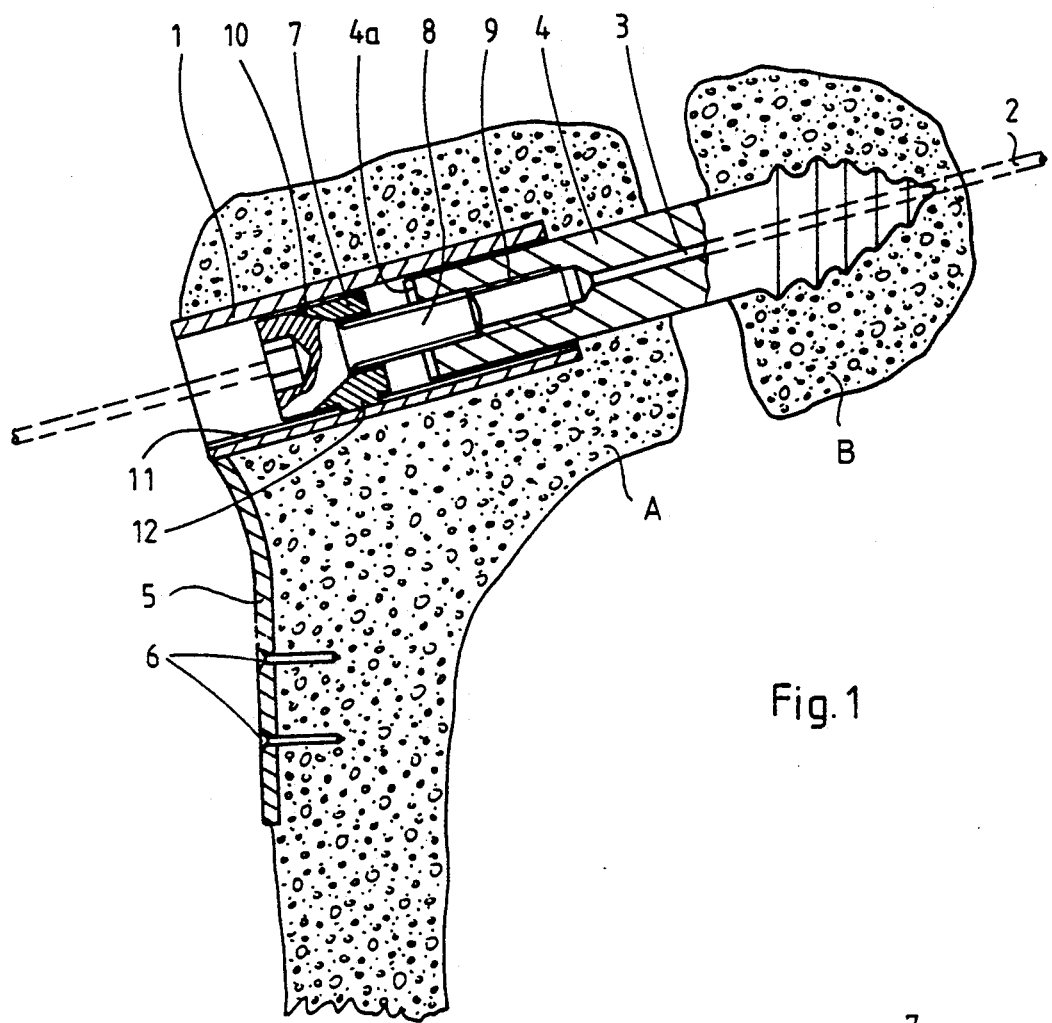
FIG. 1 is a longitudinal section of a preferred embodiment of a device for compression screwing according to the invention with a partial indication of a fracture of a femural neck.

The preferred embodiment of the device for compression screwing of the two femural neck parts A and B in FIG. 1 will be used at first to describe the method of operation:

During the operation of femural neck fractures using osteosynthesis the femur has a bore of the required diameter into which the sleeve 1 is inserted and through which a Kirschner wire 2 is then threaded as a lead. This simplifies the screwing in of the bone screw 4 which in turn has a longitudinal bore 3 through which the Kirschner wire 2 can fit.

The screw 4 is screwed through the fracture cross-section into the head part B by fitting a screwdriver into the groove 4a in the back end of the screw. The Kirschner wire 2 is then removed. The sleeve plate 5 is attached firmly to the sleeve and is fitted to the shape of the femur shaft to which it is then firmly attached by screwing cortical screws 6 into prebored holes.

Dependent on the screwing depth reached by the bone screw 4, the fixing ring 7 is positioned in the sleeve 1, whilst taking the length of a screw 8 into account which can be screwed into the inner thread 9 of the bone screw 4. The fixing ring is at first freely moveable in the sleeve. Then the compression screw 8 is screwed into the inner thread 9 at the end of the bone screw 4 which protrudes into the sleeve 1. In order for the fixing ring 7 to be able to widen whilst the compression screw 8 is being inserted both of the contact surfaces 10 of the fixing ring 7 and the bottom edge of the compression screw 8 are fitted and conical in form.

The adhesive frictional force resulting from the widening of the sleeve caused by the wedge action of the cone is greater than the compressional force acting in the longitudinal direction of the screw. In this way the sleeve is self-checking so that the bone areas A and B close in on each other in the desired fashion due to the compressional force.

Figure 2:
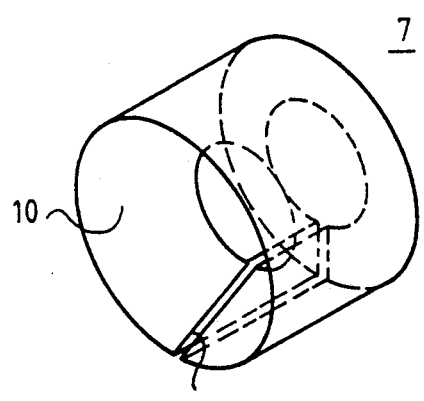
FIG. 2 is a perspective view of the fixing ring.

The sleeve 1 has a longitudinal groove 11 on the inner surface into which the pin 12 of the fixing ring 7 fits which ensures that the fixing ring 7 cannot turn whilst the compression screw 8 is being inserted. The same effect can be achieved by the fixing ring 7 as illustrated in FIG. 2 having a longitudinal slit 13 and which is inserted and moveable in the groove of the sleeve 1. The longitudinal slit 13 also improves the widening and clamping characteristics of the fixing ring 7. The implantate is totally removed after the fracture has healed.

It will be understood that the above description of the present invention is susceptible to various modifications, changes and adaptations, and the same are intended to be comprehended within the meaning and range of equivalents of the appended claims.

What is claimed is:

1. Device for compression screwing fractures of the femoral neck, consisting of a plate of a sleeve, the sleeve being hollow and cylindrical in shape, the plate of the sleeve being attached by screws to the femur shaft and of a bone screw being located within the sleeve which is provided with a female thread on its head side into which a compression screw having a respective male thread fits, whereby said compression screw is supported by means of the (bottom edge of its head (or) by a respective, especially conical contact surface) for the limitation of its movement against a fixing ring being located within said sleeve in such a way that it can be displaced, sliding with its surface along the inner surface of said sleeve and having a conical surface in an axial direction that is adapted to the bottom edge of the head of said compression screw and the cone angle of which is sized in such a way that the adhesive friction between the outer surface of the fixing ring and the inner surface of said sleeve is greater than the compressional force acting in the longitudinal direction of said compression screw.

2. Device for compression screwing as defined in claim 1, wherein said fixing ring is slit in a longitudinal direction.

3. Device for compression screwing as defined in claim 1, wherein said sleeve comprises a longitudinal guide means to prevent said fixing ring from turning in said sleeve.

4. Device for compression screwing as defined in claim 3, wherein said guide means comprises a longitudinal groove in said fixing ring into which a projection in the form of a bar on the inner surface of said sleeve slots.

5. Device for compression screwing as defined in claim 3, wherein a projection in the form of a pin is radially positioned on the outer surface of said fixing ring and which slots into a longitudinal groove on the inner surface of said sleeve.

6. Device for compression screwing as defined in claim 1, wherein all the parts of said device and all the instruments which come into contact with body tissue are constructed of the one same material, in particular, of X 5 CrNiMo 1810.

* * * * *